(12) United States Patent
Yang et al.

(10) Patent No.: US 9,097,634 B2
(45) Date of Patent: Aug. 4, 2015

(54) FLUID VISCOSITY MEASURING DEVICE

(75) Inventors: Sung Yang, Gwangju (KR); Yang-Jun Kang, Gwangju (KR)

(73) Assignees: GWANGJU INSTITUTE OF SCIENCE AND TECHNOLOGY, Gwangju (KR); NANOBIZ CO., LTD., Gwangju (KR)

( * ) Notice: Subject to any disclaimer, the term of this patent is extended or adjusted under 35 U.S.C. 154(b) by 483 days.

(21) Appl. No.: 13/580,819

(22) PCT Filed: Aug. 19, 2010

(86) PCT No.: PCT/KR2010/005498
§ 371 (c)(1),
(2), (4) Date: Oct. 23, 2012

(87) PCT Pub. No.: WO2011/105668
PCT Pub. Date: Sep. 1, 2011

(65) Prior Publication Data
US 2013/0036797 A1 Feb. 14, 2013

(30) Foreign Application Priority Data
Feb. 23, 2010 (KR) ........................ 10-2010-0016104

(51) Int. Cl.
*G01N 11/04* (2006.01)
*G01N 11/08* (2006.01)
*G01N 33/49* (2006.01)

(52) U.S. Cl.
CPC ................ *G01N 11/04* (2013.01); *G01N 11/08* (2013.01); *G01N 33/49* (2013.01)

(58) Field of Classification Search
CPC ....... G01N 11/04; G01N 11/06; G01N 11/08; G01N 2011/0066
See application file for complete search history.

(56) References Cited

U.S. PATENT DOCUMENTS

| 6,745,615 | B2 | 6/2004 | Kim et al. | |
|---|---|---|---|---|
| 2003/0106596 | A1* | 6/2003 | Yang et al. | 137/828 |
| 2006/0093488 | A1 | 5/2006 | Wong et al. | |
| 2009/0038379 | A1* | 2/2009 | Colin et al. | 73/54.01 |

FOREIGN PATENT DOCUMENTS

KR 100741262 B1 7/2007

OTHER PUBLICATIONS

Patent Abstracts of Japan; Publication No. 06-241852; Application No. 05-047338.

* cited by examiner

Primary Examiner — Paul West
(74) Attorney, Agent, or Firm — Osha • Liang LLP

(57) ABSTRACT

Disclosed is a fluid viscosity measuring device which can measure the viscosity of a fluid such as blood. The fluid viscosity measuring device of the present invention comprises: a first fluid inlet portion in which a fluid, the viscosity of which is to be measured, is injected, and a second fluid inlet portion in which a reference fluid having a standard viscosity is injected; a connection pipe configured to connect the first fluid inlet portion to the second fluid inlet portion and form a passage for the fluid, the viscosity of which is to be measured, and the reference fluid; a plurality of counting channels in communication with the connection pipe at a predetermined distance to be filled with the two fluids flowing along the passage, respectively; and a boundary surface measuring unit configured to count the counting channels filled with the two fluids, respectively.

11 Claims, 11 Drawing Sheets a) $Q_A : Q_B = 100:100$ μL/h b) $Q_A : Q_B = 100:1000$ μL/h a) $Q_A : Q_B = 200:200$ μL/h b) $Q_A : Q_B = 400:200$ μL/h c) $Q_A : Q_B = 600:200$ μL/h d) $Q_A : Q_B = 800:200$ μL/h e) $Q_A : Q_B = 1000:200$ μL/h f) $Q_A : Q_B = 1200:200$ μL/h g) $Q_A : Q_B = 1400:200$ μL/h h) $Q_A : Q_B = 2000:200$ μL/h a) $Q_A:Q_B=1000:1000$ uL/h b) $Q_A:Q_B=750:1000$ uL/h a) $Q_A:Q_B=1000:1000$ uL/h b) $Q_A:Q_B=620:1000$ uL/h a) $Q_A:Q_B=1000:1000$ uL/h b) $Q_A:Q_B=490:1000$ uL/h a) $Q_A:Q_B$=1000:1000 uL/h    b) $Q_A:Q_B$=430:1000 uL/h

FLUID VISCOSITY MEASURING DEVICE

TECHNICAL FIELD

The present invention relates to a viscometer, and more particularly, to a fluid viscosity measuring device that can measure the viscosity of a fluid such as blood.

BACKGROUND ART

In general, a fluid viscosity measuring device configured to measure the viscosity of a fluid such as blood is referred to as a viscometer. Kinds of viscometers widely used so far include a capillary viscometer, a rotary viscometer, etc. However, typical viscometers such as a capillary viscometer or a rotary viscometer have problems in that the consumption amount (approximately a milliliter) of a sample is relatively high, a great deal of measurement time (approximately 1 hour) is required, and measurement errors are relatively frequent. On the other hand, a microfluidic device-based viscometer has advantages such as a relatively small consumption amount (approximately a microliter) of a sample, a short measurement time (approximately several minutes), and accurate real-time evaluation of repetitiveness and reproducibility, and thus its research has been widely conducted. Such a microfluidic viscometer is essentially required to analyze accurate rheological properties. In particular, the microfluidic viscometer is considered to be one of analytic tools in the field of applications such as chemistry, biology and biomedical engineering. There is an increasing demand for equipment that can rapidly and accurately measure viscosity due to the necessity and availability of the microfluidic viscometer.

To measure the viscosity of a target fluid using a microfluidic device, various methods using a pressure drop due to friction loss caused by fluid flow of a target fluid have been proposed. The methods proposed in the related art are classified into two groups: "a) a method of directly measuring viscosity using a pressure sensor, and b) a method of indirectly measuring viscosity using a change in boundary surface according to a viscosity ratio between two fluids. First, the method of directly measuring viscosity using a pressure sensor essentially requires complicated calibration and correction. On the other hand, the method of indirectly measuring viscosity using a change in boundary surface according to a viscosity ratio between two fluids can be used to easily measure viscosity without using a pressure sensor. However, since the shape of the boundary surface may be widely changed according to the viscosity ratio or a surface tension ratio between two fluids, such a method requires calibration and correction to accurately detect the boundary surface of the target fluid, and requires image processing as well.

DISCLOSURE

Technical Problem

The present invention is designed to solve the problems of the prior art, and therefore it is an object of the present invention to provide a fluid viscosity measuring device that can accurately measure the viscosity of a target fluid using a microchannel array having a plurality of counting channels without the need for complicated calibration or correction.

These objects of the present invention are not limited to the objects as described above. Therefore, it should be understood that the other objects of the present invention which are not described herein be clearly apparent from the following description.

Technical Solution

To achieve the objects of the present invention, a fluid viscosity measuring device according to a preferred example embodiment of the present invention may include a first fluid inlet portion through which a target fluid whose viscosity is to be measured is injected, and a second fluid inlet portion through which a reference fluid having a reference viscosity is injected and, a connection pipe configured to connect the first fluid inlet portion and the second fluid inlet portion with each other and form passages for the target fluid and the reference fluid, a plurality of counting channels disposed in communication with the connection pipe at a predetermined distance to be filled with the target fluid and the reference fluid which flow respectively through the passages of the connection pipe, and a boundary surface measuring unit configured to count the counting channels filled with either the target fluid or the reference fluid.

The counting channels may be formed at the connection pipe in a vertical direction.

Also, in the fluid viscosity measuring device according to the present invention, a normalized relative viscosity ratio ($[m_A/m_B]_{expected}/[m_A/m_B]_{known}$, wherein $[m_A/m_B]$ represents a relative viscosity ratio between a target fluid A and a reference fluid B, and the subscripts "known and expected" represent a known value and an expected value, respectively) between the target fluid and the reference fluid may be convergent to 1 by increasing the fluidic resistance ratio between the connection pipe and the counting channels.

In addition, the fluid resistance of the connection pipe may be set to be at least 1,000 times, and, more preferably 3,000 times, lower than those of the counting channels so that most of the friction loss of the target fluid and the reference fluid can take place in the counting channels.

Additionally, the fluid viscosity measuring device according to the present invention may measure the viscosity of the target fluid using a number ratio of the counting channels filled with the target fluid and the reference fluid, and an injection flow rate ratio between the target fluid and the reference fluid. Here, the viscosity of the target fluid may be expressed as a function of the injection flow rates of the target fluid and the reference fluid and the number of the counting channels filled with either the target fluid or the reference fluid. More particularly, a viscosity coefficient of the target fluid may be calculated based on the following mathematical equation:

$$\mu_A = \mu_B \left(\frac{N_A}{N_B}\right)\left(\frac{Q_B}{Q_A}\right)$$

In the mathematical equation, $\mu_A$ and $\mu_B$ represent viscosity coefficients of the target fluid and the reference fluid, respectively, $N_A$ and $N_B$ represent the numbers of the counting channels filled with the target fluid and the counting channels filled with the reference fluid, respectively, and $Q_A$ and $Q_B$ represent injection flow rates of the target fluid and the reference fluid, respectively.

The target fluid may include a non-Newtonian fluid whose viscosity varies according to a shear rate, and the reference fluid may include a Newtonian fluid having a constant viscosity regardless of the shear rate. For example, the target fluid may be blood, and the reference fluid may be phosphate buffered saline (PBS).

Also, both of the target fluid and the reference fluid may include a Newtonian fluid having a constant viscosity regardless of the shear rate. For example, the target fluid may be a sodium dodecyl sulfate (SDS) solution, and the reference fluid may be deionized (DI) water.

The boundary surface measuring unit may include a first electrode provided in one of the counting channels filled with the target fluid, and a first resistance detection unit electrically connected with the first electrode to detect resistance of the first electrode, a second electrode provided in one of the counting channels filled with the reference fluid, and a second resistance detection unit electrically connected with the second electrode to detect resistance of the second electrode, and a third electrode provided in one of the counting channels arranged between the first electrode and the second electrode so as to detect a fixed boundary surface between the target fluid and the reference fluid while allowing the boundary surface between the two fluids to move by changing the injection flow rate ratio between the two fluids, and a third resistance detection unit electrically connected with the third electrode to detect resistance of the third electrode.

Also, the fluid viscosity measuring device according to the present invention may include a first fluid inlet portion through which a target fluid whose viscosity is to be measured is injected, and a second fluid inlet portion through which a reference fluid having a reference viscosity is injected, a connection pipe configured to connect the first fluid inlet portion and the second fluid inlet portion with each other and form passages for the target fluid and the reference fluid, and a plurality of counting channels disposed in communication with the connection pipe at a predetermined distance to be filled with the target fluid and the reference fluid which flow respectively through the passages of the connection pipe. Here, it is characterized in that fluid resistance of the connection pipe may be set to be at least 1,000 times lower than those of the counting channels so that most of the friction loss of the target fluid and the reference fluid can take place in the counting channels.

Specific details of the other example embodiments are included in the detailed description and shown in the accompanying drawings.

Advantageous Effects

According to the fluid viscosity measuring device of the present invention as described above, the number of counting channels filled with a reference fluid and a target fluid is varied due to a relative difference in viscosities of the reference fluid having a reference viscosity and the target fluid whose viscosity is to be measured such as blood, and then a variation in the number of counting channels can be measured using a change in electric resistance. Accordingly, it is possible to easily measure the viscosity of the target fluid. That is, the fluid viscosity measuring device according to the present invention can be useful in accurately measuring viscosity of a target fluid using a microchannel array having a plurality of counting channels without the need for complicated calibration or correction.

Also, not only a Newtonian fluid but also a fluid having a non-Newtonian behavior such as blood may be simply and accurately measured for viscosity at various shear rates.

The effects of the present invention are not limited to the effects as described above. Therefore, it should be understood that the other effects of the present invention which are not described herein be clearly described within the scope of the appended claims, as apparent to those skilled in the art.

BEST MODE

Figure 1:
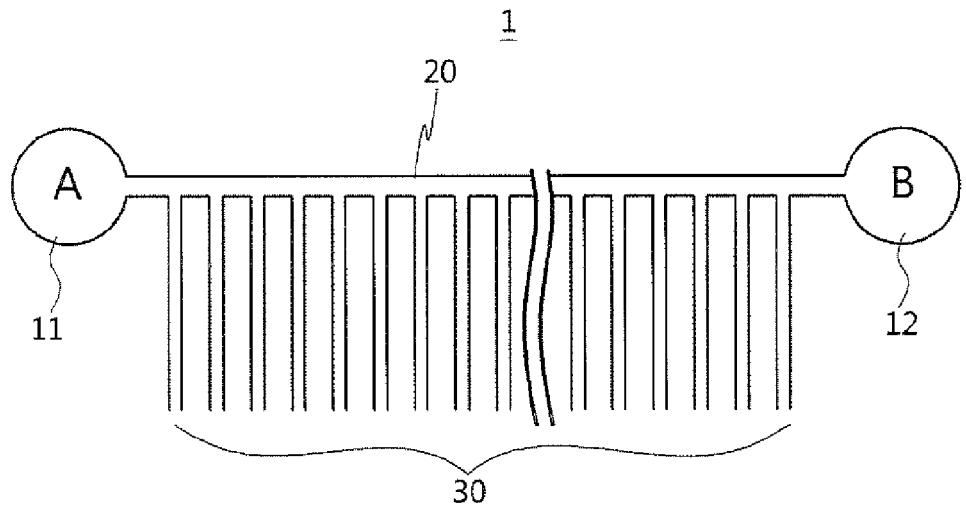
FIG. 1 is a schematic diagram of a fluid viscosity measuring device according to a preferred example embodiment of the present invention.

The features and advantages of the present invention and methods of achieving the features and advantages of the present invention will become more apparent to those of ordinary skill in the art by describing in detail exemplary example embodiments thereof with reference to the attached drawings. However, it should be understood that specific structural and functional details disclosed herein are merely representative for purposes of describing example embodiments of the present invention, however, example embodiments of the present invention may be embodied in many alternate forms and should not be construed as limited to example embodiments of the present invention set forth herein. Accordingly, while the invention is susceptible to various modifications and alternative forms, specific example embodiments thereof are shown by way of example in the drawings and will herein be described in detail. It should be understood, however, that there is no intent to limit the invention to the particular fauns disclosed, but on the contrary, the invention is to cover all modifications, equivalents, and alternatives falling within the spirit and scope of the invention. Like numbers refer to like elements throughout the description of the figures.

Hereinafter, the fluid viscosity measuring device according to the preferred example embodiment will be described in detail with reference to the attached drawings. For example, when specific description of known related functions or components in the detailed description of the present invention are considered to depart from the scope of the present invention, the detailed description of the related functions or components are omitted for clarity.

FIG. 1 is a schematic diagram of a fluid viscosity measuring device according to a preferred example embodiment of the present invention.

As shown in FIG. 1, the fluid viscosity measuring device 1 according to a preferred example embodiment of the present invention may include fluid injection ports 11 and 12, a connection pipe 20 and counting channels 30.

The fluid injection port may include a first fluid inlet portion 11 through which a target fluid A whose viscosity is to be measured is injected, and a second fluid inlet portion 12 through which a reference fluid B having a reference viscosity is injected.

Here, a Newtonian fluid which is not mixed with the target fluid A and having a constant viscosity regardless of a shear rate, is used as the reference fluid B having a known viscosity. According to one example embodiment of the present invention, when the target fluid A is a non-Newtonian fluid whose viscosity varies according to the shear rate, for example, blood, a phosphate buffered saline (PBS) having Newtonian behavior, is preferably used as the reference fluid B. Also, when the target fluid A is a Newtonian fluid having a constant viscosity regardless of the shear rate, for example, a sodium dodecyl sulfate (SDS) solution, deionized (DI) water having Newtonian behavior, is preferably used as the reference fluid B. That is, the fluid viscosity measuring device 1 according to the present invention can measure the viscosity of the Newtonian fluid having a constant viscosity regardless of the shear rate and the viscosity of the non-Newtonian fluid whose viscosity varies according to the shear rate at the same time.

Also, a pump (not shown) and valves (not shown) may be provided to inject the target fluid A and the reference fluid B through the first fluid inlet portion 11 and the second fluid inlet portion 12, respectively.

The connection pipe 20 connects the first fluid injection port 11 and the second fluid injection port 12 with each other. The connection pipe 20 is provided in a tubular shape in which passages for the target fluid A and the reference fluid B are formed in the connection pipe 20. According to one example embodiment of the present invention, the connection pipe 20 is provided in a cubical shape with rectangular cross sections, but may be provided in the form of circular and polygonal cross sections unlike the present invention.

The counting channels 30 may be provided in plural numbers so that the counting channels 30 can be disposed in communication with the connection pipe 20 at a predetermined distance to be filled with the target fluid A and the reference fluid B which flow respectively through the passages of the connection pipe 20. The counting channels 30 are disposed at the connection pipe 20 in a direction parallel with the flow direction of the target fluid A and the reference fluid B, that is, in a direction perpendicular to the connection pipe 20, and plays such a role that the flow characteristics of the target fluid A and the reference fluid B, particularly, the viscosities of the two fluids A and B, are determined in the counting channels 30 under the condition in which the fluid resistances of the counting channels 30 are relatively higher than that of the connection pipe 20. Such counting channels 30 can be manufactured, using a microelectromechanical system (MEMS), so that each counting channel has a rectangular or certain cross section.

Figure 2:
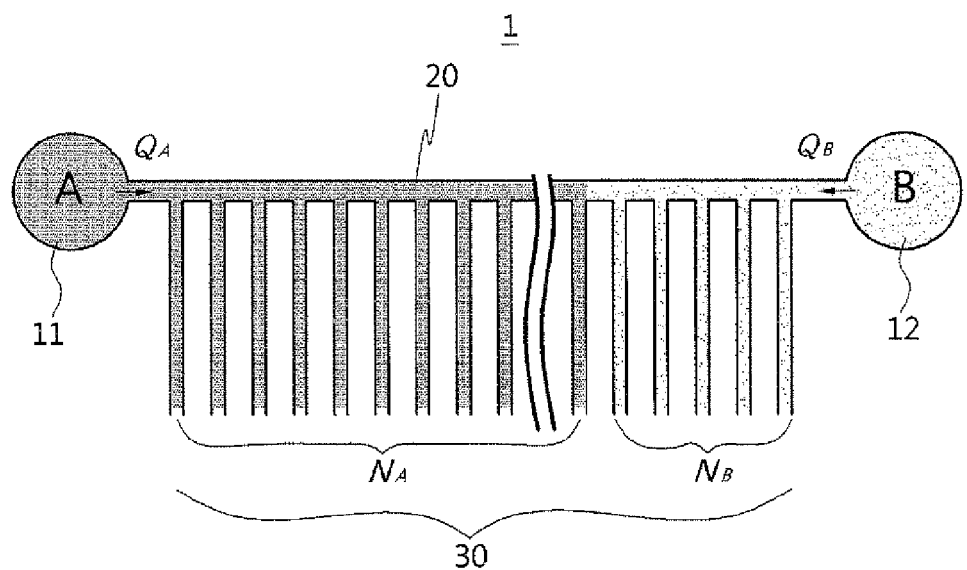
FIG. 2 is a diagram for explaining the principle of measuring the viscosity of a fluid using the fluid viscosity measuring device according to the present invention.

FIG. 2 is a diagram for explaining the principle of measuring the viscosity of a fluid using the fluid viscosity measuring device according to the present invention. As shown in FIG. 2, the channel numbers of the counting channels 30 filled with the target fluid A and the reference fluid B are varied depending on a pressure drop due to friction loss caused by a relative difference in viscosities of the target fluid A and the reference fluid B. The viscosity ($m_A$) of the target fluid A may be calculated using these parameters, that is, using the numbers ($N_A$ and $N_B$) of the counting channels 30 filled with the target fluid A and the reference fluid B, and the injection flow rates ($Q_A$ and $Q_B$) of the target fluid A and the reference fluid B.

Figure 3:
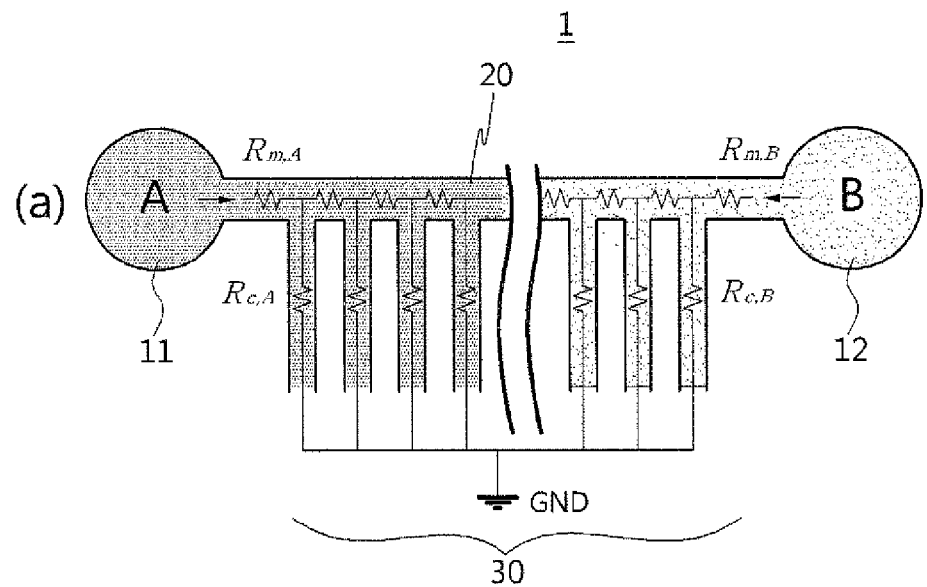
FIG. 3 is a diagram for explaining the mathematical modeling of the fluid viscosity measuring device according to the present invention.
Figure 3:
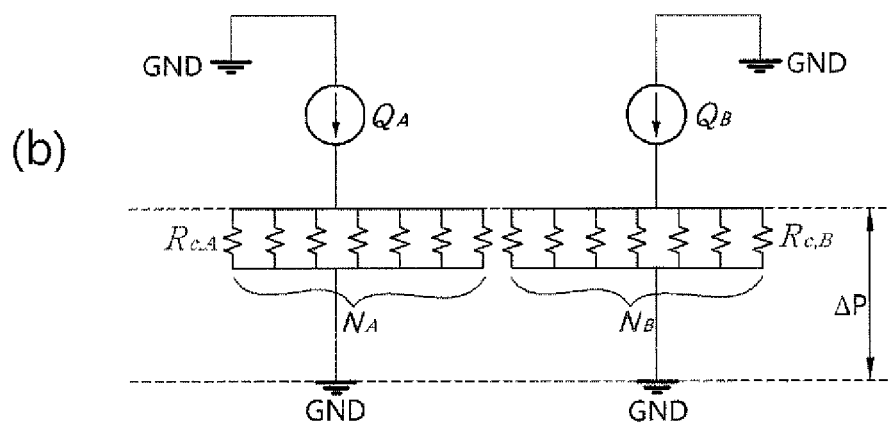

FIG. 3 is a diagram for explaining the mathematical modeling of the fluid viscosity measuring device according to the present invention.

As shown in FIG. 3, the viscosity ($m_A$) of the target fluid A is determined using the viscosity ($m_B$) of the reference fluid B, the numbers ($N_A$ and $N_B$) of the counting channels 30 filled with the target fluid A and the reference fluid B, and the injection flow rates ($Q_A$ and $Q_B$) of the target fluid A and the reference fluid B.

Injection flow rate and fluid resistance may be simply expressed as electric current and resistance, respectively, using the similarity law. Here, FIG. 3A shows the mathematical modeling in consideration of the fluid resistances ($R_{m,A}$ and $R_{m,B}$) which are generated in the connection pipe 20 due to injection of the target fluid A and the reference fluid B. When the connection pipe 20 is designed instead of this modeling so that a pressure drop in the connection pipe 20 caused by the friction loss of the target fluid A and the reference fluid B is ignored, a certain pressure drop in the counting channels 30 vertically disposed at the connection pipe 20 is caused as shown in FIG. 3B. Therefore, the relational expression between the viscosity ($m_A$) of the target fluid A and the viscosity ($m_B$) of the reference fluid B may be simply deduced, and may be expressed using the numbers ($N_A$ and $N_B$) of the counting channels 30 filled with the target fluid A and the reference fluid B, and the injection flow rates ($Q_A$ and $Q_B$) of the target fluid A and the reference fluid B.

That is, when the relational expression for the viscosity ($m_A$) of the target fluid A is in consideration of the Poiseuille flow characteristics widely known in the art, relational expressions (2) and (3) for the pressure drops (DPs) and the flow rates (Qs) of the target fluid A and the reference fluid B are deduced from relational expression (1) for the pressure drop (DP) and the flow rate (Q):

$$\Delta P = R_f Q \qquad (1)$$

$$\Delta P_A = \left(\frac{R_A}{N_A}\right) Q_A \qquad (2)$$

$$\Delta P_B = \left(\frac{R_B}{N_B}\right) Q_B \qquad (3)$$

Since the pressure drop (DP) is the same in relational expressions (1) to (3), relational expression (4) is deduced from relational expressions (2) and (3).

$$\left(\frac{R_A}{N_A}\right) Q_A = \left(\frac{R_B}{N_B}\right) Q_B \qquad (4)$$

In this case, relational expression (6) is deduced by applying relational expression (5) for the fluid resistance against a channel having a low aspect ratio to relational expression (4).

$$R_f = \left(\frac{12\mu L}{wh^3}\right) \qquad (5)$$

$$\left(\frac{12\mu_A L}{wh^3}\right)\left(\frac{Q_A}{N_A}\right) = \left(\frac{12\mu_B L}{wh^3}\right)\left(\frac{Q_B}{N_B}\right) \qquad (6)$$

Since a channel height h, a length L and a width w are the same in relational expression (6), relational expression (6) may be simply defined as shown in relational expression (7).

$$\left(\frac{\mu_A Q_A}{N_A}\right) = \left(\frac{\mu_B Q_B}{N_B}\right) \qquad (7)$$

Accordingly, the viscosity ($m_A$) of the target fluid A may be calculated based on relational expression (8).

$$\mu_A = \mu_B \left(\frac{N_A}{N_B}\right)\left(\frac{Q_B}{Q_A}\right) \qquad (8)$$

In relational expression (8), $\mu_A$ and $\mu_B$ represent viscosity coefficients of the target fluid A and the reference fluid B, respectively, $N_A$ and $N_B$ represent the numbers of the counting channels 30 filled with the target fluid A and the counting channels 30 filled with the reference fluid B, respectively, and $Q_A$ and $Q_B$ represent injection flow rates of the target fluid A and the reference fluid B, respectively.

When relational expression (8) is expressed as shown in relational expression (9), the relative viscosity ratio ($m_A/m_B$) between the two fluids A and B means a slope of the injection flow rate ratio ($Q_A/Q_B$) between the two fluids A and B with respect to the number ratio ($N_A/N_B$) of the counting channels 30 filled with the target fluid A and the reference fluid B.

$$\left(\frac{\mu_A}{\mu_B}\right) = \frac{\left(\frac{N_A}{N_B}\right)}{\left(\frac{Q_A}{Q_B}\right)} \qquad (9)$$

Relational expression (9) is deduced under the condition in which the friction loss in the connection pipe 20 may be relatively ignored compared with those of the counting channels 30. To find the requirements satisfying this assumption, relational expression (9) may be schematically expressed as shown in FIG. 4.

Figure 4:
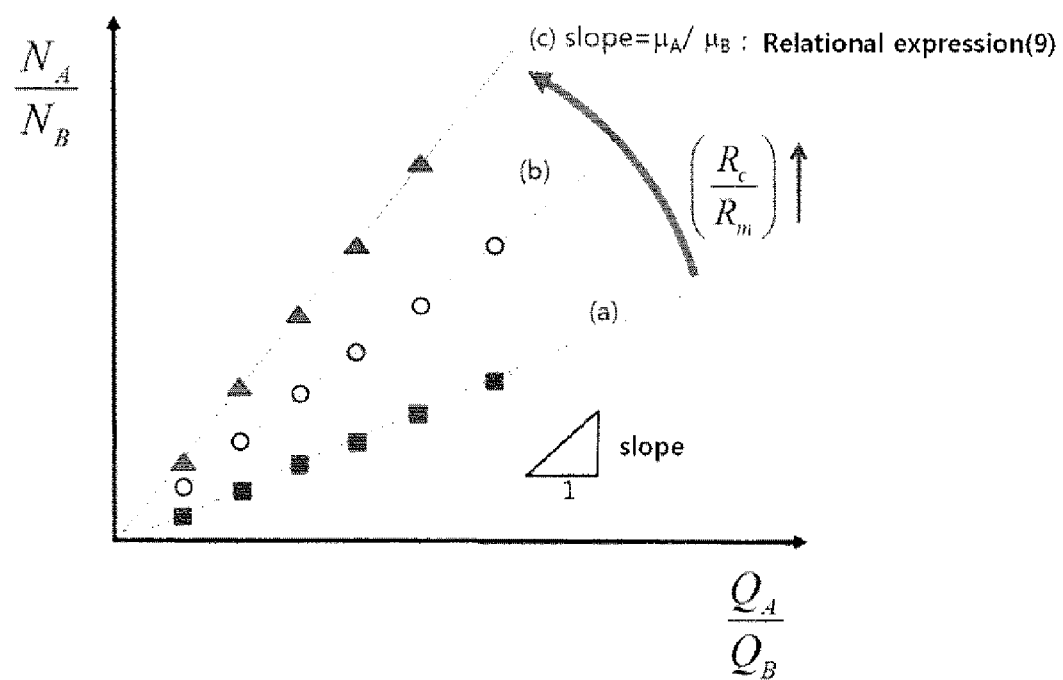
FIG. 4 is a graph for theoretically explaining a channel number ratio ($N_A/N_B$) of counting channels filled with a target fluid A and a reference fluid B according to an injection flow rate ratio ($Q_A/Q_B$) between the fluid A and the reference fluid B.

FIG. 4 is a graph for theoretically explaining a channel number ratio ($N_A/N_B$) of the counting channels 30 filled with the target fluid A and the reference fluid B according to an injection flow rate ratio ($Q_A/Q_B$) between the fluid A and the reference fluid B.

Referring to FIG. 4, Cases (a) and (b) have a relatively lower slope than Case (c) which satisfies the requirements of the relational expression (9). Here, the slope means the relative viscosity ratio ($m_A/m_B$) between the two fluids A and B. This is caused by friction loss in the connection pipe 20. To solve this problem, fluid resistance of the connection pipe 20 should be low. That is, the requirements satisfying relational expression (9) may be achieved by increasing the fluidic resistance ratio between the connection pipe 20 and the counting channels 30.

Figure 5:
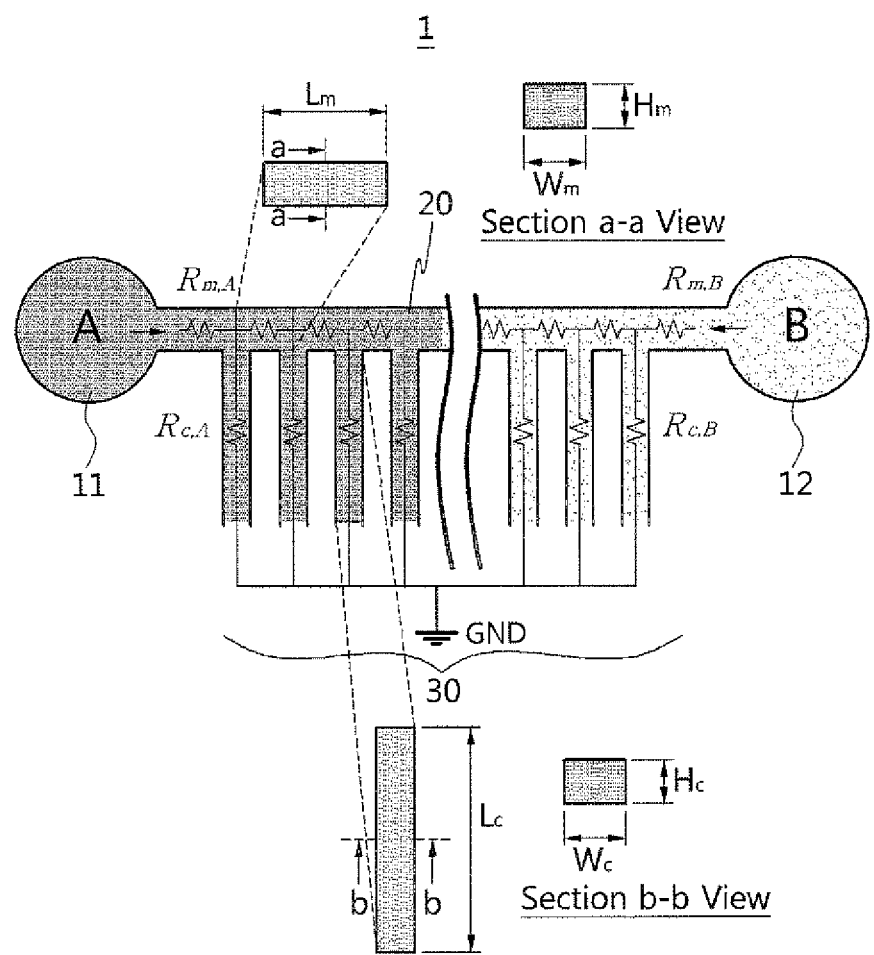
FIG. 5 is a diagram for explaining the parameters ($L_m$, $W_m$, and $H_m$) regarding fluid resistance of a connection pipe, and the parameters ($L_c$, $W_c$, and $H_c$) regarding fluid resistances of the counting channels.

FIG. 5 is a diagram for explaining the parameters ($L_m$, $W_m$, and $H_m$) regarding the fluid resistance of the connection pipe, and the parameters ($L_c$, $W_c$, and $H_c$) regarding the fluid resistances of the counting channels.

As shown in FIG. 5, the fluid resistances (Rs) of the connection pipe 20 and the counting channels 30 are affected by the parameters such as cross section area (width W and height H) and length L. The fluidic resistance ratio ($R_c/R_m$, fluid resistance of counting channels/fluid resistance of connection pipe) between the connection pipe 20 and the counting channels 30 is deduced as relational expression (10) using relational expression (5) for fluid resistance.

$$\left(\frac{R_c}{R_m}\right) = \left(\frac{L_c}{L_m}\right)\left(\frac{W_m}{W_c}\right)\left(\frac{H_m}{H_c}\right)^3 \quad (10)$$

In relational expression (10), $L_c$, $W_c$, and $H_c$ represent a length, a width, and a height of the counting channel 30, and $L_m$, $W_m$, and $H_m$ represent a length, a width, and a height of the connection pipe 20. That is, according to relational expression (10) for the fluidic resistance ratio, the effect of the heights $H_m$ and $H_c$ of the connection pipe 20 and the counting channels 30 is relatively high, and the fluidic resistance ratio ($R_c/R_m$) may be calculated from relational expression (10).

Figure 6:
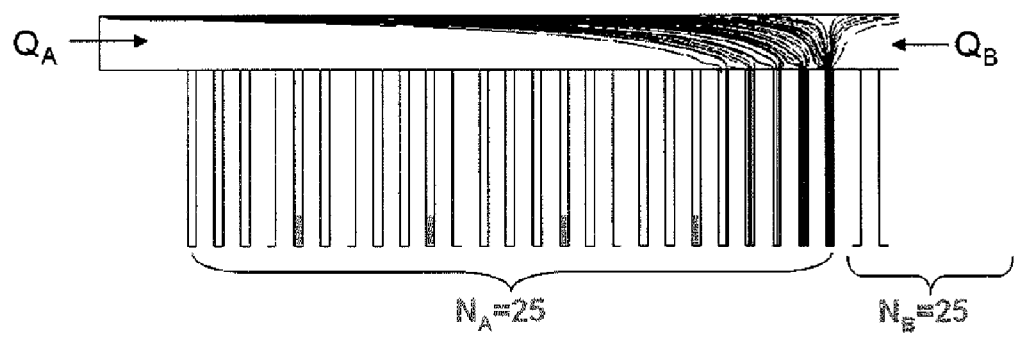
FIG. 6 is a diagram showing the numerical analysis results of the channel number of filled counting channels according to a change in injection flow rate ratio between the target fluid and the reference fluid, both of which have the same viscosity ($m_A = m_B$), in the fluid viscosity measuring device satisfying a fluidic resistance ratio ($R_c/R_m$) between the connection pipe and the counting channels.
Figure 6:
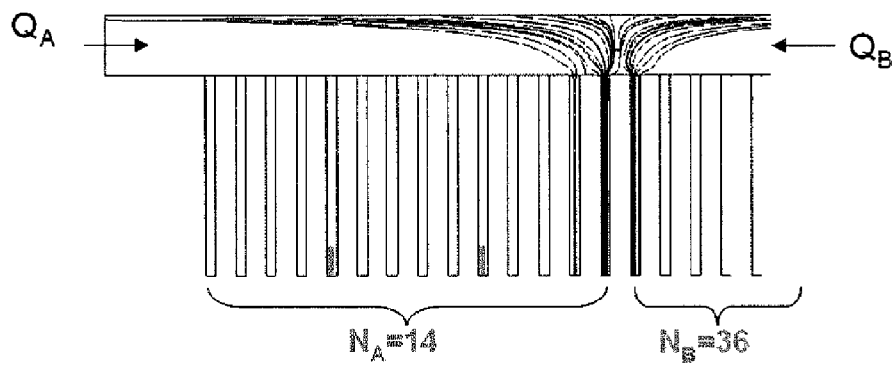

FIG. 6 is a diagram showing the numerical analysis results of the channel numbers of the counting channels 30 filed with the target fluid A and the reference fluid B according to the change in injection flow rate ratio between the target fluid A and the reference fluid B, both of which have the same viscosity ($m_A=m_B$), in the fluid viscosity measuring device 1 which is designed so that the number of counting channels 30 and the fluidic resistance ratio ($R_c/R_m$) between the connection pipe 20 and the counting channels 30 are 50 and 116, respectively.

According to the numerical analysis results, the number of the counting channels 30 filled with the two fluids A and B are the same at 25 under the same flow rate condition ($Q_A=Q_B$) as shown in FIG. 6A. In FIG. 6B, however, the injection flow rate ($Q_B$) of the reference fluid B is 10 times higher than the injection flow rate ($Q_A$) of the target fluid A, but the channel number ($N_A$) of the counting channels 30 filled with the target fluid A and the number ($N_B$) of the counting channels 30 filed with the reference fluid B are 14 and 36, respectively. That is, the channel number ratio ($N_B/N_A$) of the counting channels 30 filed with the target fluid A and the reference fluid B is 2.6 when the flow rate ratio ($Q_B/Q_A$) is 10. Therefore, considering that the channel number ratio should be 10 when there is no friction loss in the connection pipe 20, the designed fluid viscosity measuring device has problems in that a great deal of friction loss is caused in the connection pipe, and thus a lot of measurement errors are necessarily caused when viscosity is calculated using relational expression (9).

As a result, an increase in fluidic resistance ratio between the connection pipe 20 and the counting channels 30 is required to reduce the effect on the friction loss caused in the connection pipe 20.

Figure 7:
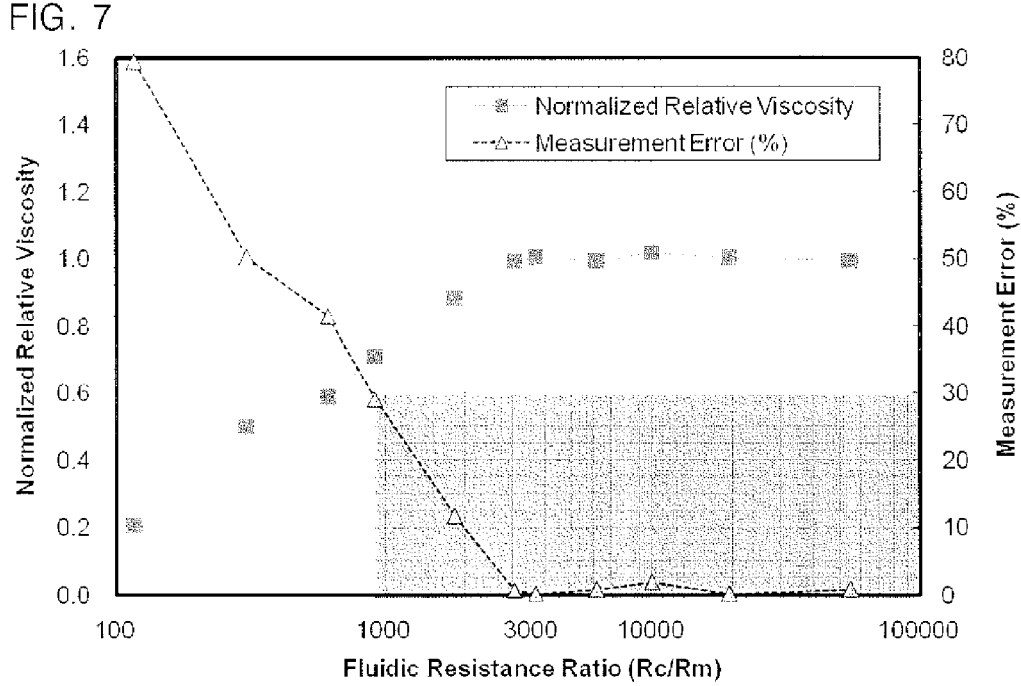
FIG. 7 is a graph illustrating the relationship between measurement error and normalized relative viscosity ($[m_A/m_B]_{expected}/[m_A/m_B]_{known}$, wherein $[m_A/m_B]$ represents a relative viscosity ratio between a target fluid A and a reference fluid B, and the subscripts "known and expected" represent a known value and an expected value, respectively) according to the fluidic resistance ratio between the connection pipe and the counting channels.

First, the two fluids A and B are set using the same viscosity condition ($m_A=m_B$), and the numerical analysis results for the relative viscosity ($m_A/m_B$) that is the slope of the injection flow rate ratio ($Q_A/Q_B$) between the two fluids A and B with respect to the channel number ratio ($N_A/N_B$) of the counting channels 30 filled with the two fluids A and B as shown in relational expression (9), is obtained due to an increase in fluidic resistance ratio ($R_c/R_m$), as shown in FIG. 7.

FIG. 7 is a graph illustrating the relationship between measurement error and normalized relative viscosity ($[m_A/m_B]_{expected}/[m_A/m_B]_{known}$, wherein $[m_A/m_B]$ represents a relative viscosity ratio between the target fluid A and the reference fluid B, and the subscripts "known and expected" represent a known value and an expected value, respectively) according to the fluidic resistance ratio between the connection pipe and the counting channels.

According to numerical analysis results obtained with reference to FIG. 7, the more the fluid resistance ratio (RJR.) increases, the closer the normalized relative viscosity ($[m_A/m_B]_{expected}/[m_A/m_B]_{known}$) is to 1, and the more errors in calculation of the viscosity are reduced. That is, the effect of friction loss in the connection pipe 20 may be further reduced.

When the fluidic resistance ratio ($R_c/R_m$) exceeds 3,000, normalized relative viscosity ($[m_A/m_B]_{expected}/[m_A/m_B]_{known}$) is convergent to 1, and an error frequency in calculation of viscosity using relational expression (9) is less than 1%, which indicates that viscosity can be accurately measured. Since the viscosity measurement error is convergent to less than 1% when the fluidic resistance ratio ($R_c/R_m$) exceeds 3,000, it is unnecessary to set its upper limit. Accordingly, it is desirable to set an upper limit of the fluidic resistance ratio ($R_c/R_m$) to less than 100.

From the results as described above, it is desirable to set the fluidic resistance ratio ($R_c/R_m$) between the connection pipe 20 and the counting channels 30 to 1,000 or more so that a proposed measurement error of the fluid viscosity measuring device 1 is at least 30% or less. That is, the fluid resistance ($R_m$) of the connection pipe 20 is set to be at least 1,000 times lower than the fluid resistance ($R_c$) of the counting channels 30 so that friction loss of the target fluid A and the reference fluid B can be reduced in the connection pipe 20 and most of the counting channels 30. Here, the fluidic resistance ratio ($R_c/R_m$) is determined by the six parameters ($L_c$, $W_c$, $H_c$, $L_m$, $W_m$, and $H_m$) as shown in relational expression (10).

Figure 8:
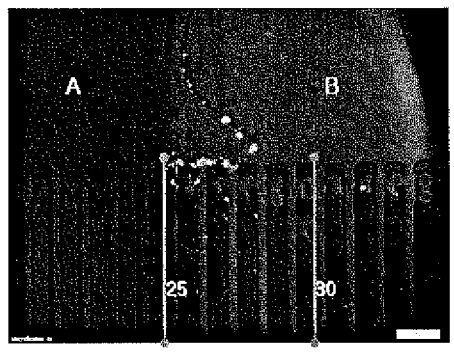
FIG. 8 is a diagram showing images taken to detect the number of counting channels filled respectively with two fluids having the same viscosity according to a change in flow rate ratio between the two fluids so as to experimentally verify the theoretical relational expression derived using the fluid viscosity measuring device according to the present invention.
Figure 8:
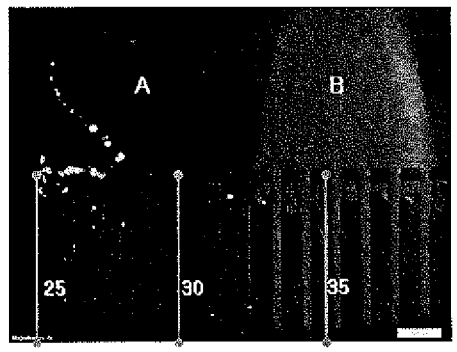
Figure 8:
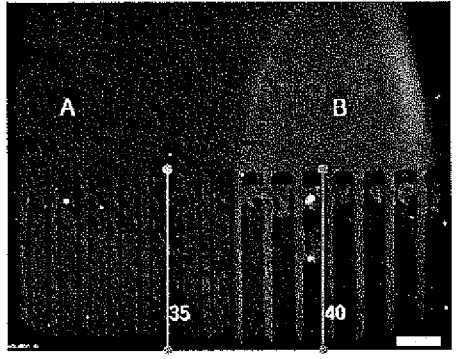
Figure 8:
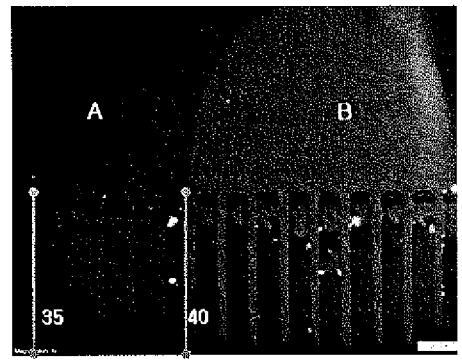
Figure 8:
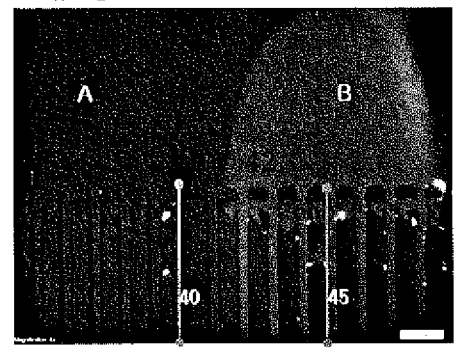
Figure 8:
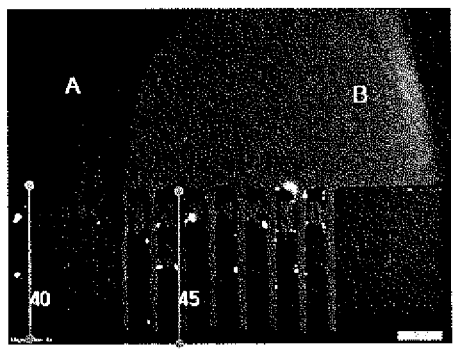
Figure 8:
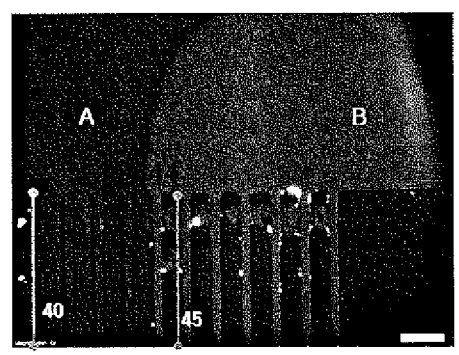
Figure 8:
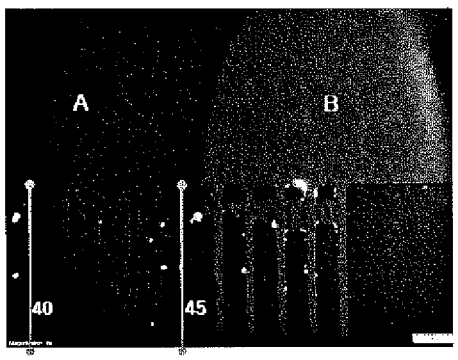

FIG. 8 shows the images taken under a microscope to detect the number of the counting channels 30 filled respectively with the target fluid A and the reference fluid B, both of which have the same viscosity ($m_A=m_B$), when the injection flow rate ($Q_B$) of the reference fluid B is fixed at 200 mL/h and the injection flow rate ($Q_A$) of the target fluid A is set to 200 to 2,000 mL/h so as to experimentally verify relational expression (8) for the viscosity derived using the fluid viscosity measuring device in which the fluidic resistance ratio ($R_c/R_m$) between the connection pipe 20 and the counting channels 30 is set to 6,300.

Figure 9:
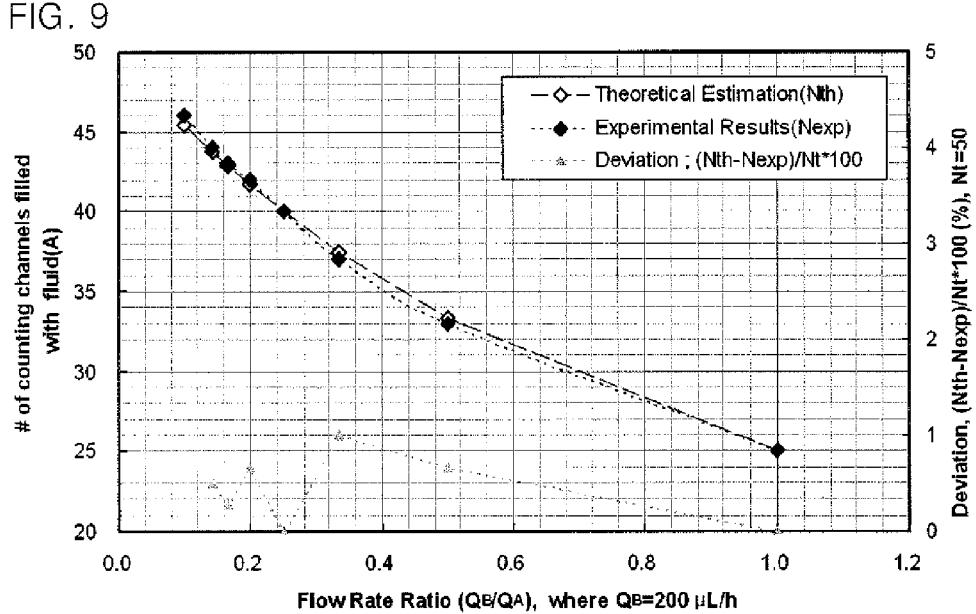
FIG. 9 is a graph illustrating the theoretical estimation and experimental results of the channel number of the counting channels filled with the target fluid according to an injection flow rate ratio between the target fluid and the reference fluid, and a deviation between the theoretical estimation and the experimental results.

FIG. 9 is a graph illustrating the experimental and theoretical results of the channel number ($N_A$) of the counting channels 30 filled with the target fluid A according to the flow rate ratio ($Q_B/Q_A$) between the target fluid A and the reference fluid B using the experimental results shown in FIG. 8, and a deviation between the experimental and theoretical estimation results. That is, it is revealed that the experimental and theoretical estimation results fall within 1% in average, which indicates the desirable accuracy of measurement.

Figure 10:
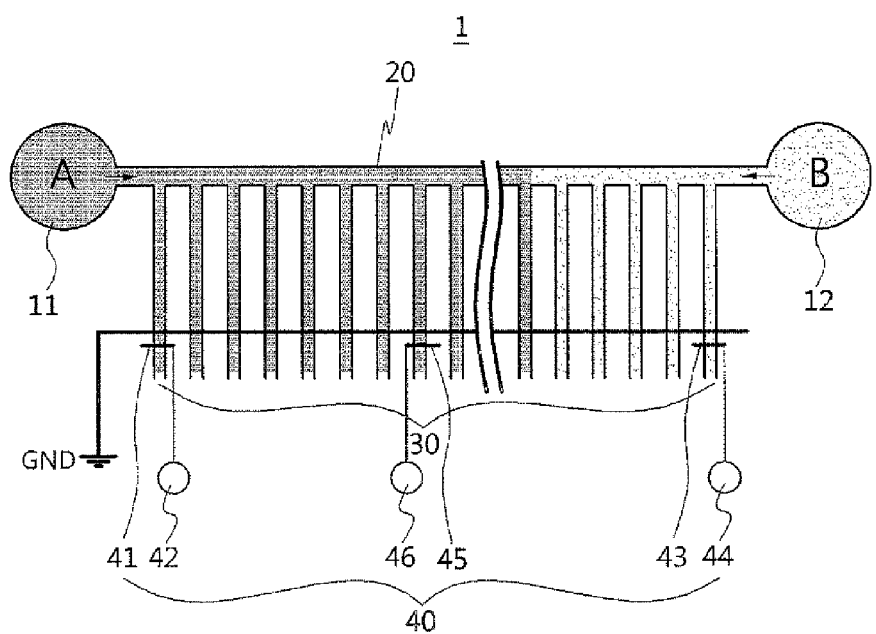
FIG. 10 is a diagram for explaining a method of measuring the viscosity of the target fluid by adjusting the injection flow rate ratio between the target fluid and the reference fluid to fix the channel numbers of the counting channels at a predetermined ratio.

FIG. 10 is a diagram for explaining a method of measuring the viscosity of the target fluid by adjusting the injection flow rate ratio between the target fluid and the reference fluid so as to fix the channel numbers of the counting channels filled with the target fluid and the reference fluid at a predetermined ratio.

As shown in FIG. 10, the fluid viscosity measuring device 1 according to the preferred example embodiment of the present invention may include a boundary surface measuring unit 40 configured to count the counting channels 30 filled with either the target fluid A or the reference fluid B.

The boundary surface measuring unit 40 may include a target fluid measuring unit, a reference fluid measuring unit and a fixed boundary surface measuring unit.

Here, the target fluid measuring unit includes a first electrode 41 provided in one of the counting channels 30 filled with the target fluid A, and a first resistance detection unit 42 electrically connected with the first electrode 41 to detect the resistance of the first electrode 41. Also, the reference fluid measuring unit includes a second electrode 43 provided in one of the counting channels 30 filled with the reference fluid B, and a second resistance detection unit 44 electrically connected with second electrode 43 to detect the resistance of second electrode 43. In addition, the fixed boundary surface measuring unit includes a third electrode 45 provided in one of the counting channels 30 arranged between the first electrode 41 and the second electrode 43 so as to detect a fixed boundary surface between the target fluid A and the reference fluid B while allowing the boundary surface between the two fluids A and B to move by changing the injection flow rate ratio between the two fluids A and B, and a third resistance detection unit 46 electrically connected with the third electrode 45 to detect the resistance of the third electrode 45.

In general, resistance may be accurately detected for each of the counting channels 30 since the electric resistance varies according to the kind of target fluid A. For this purpose, the number of counting channels 30 and an equivalent number of resistance detection units are required. Therefore, this is very inefficient since a large number of resistance detection units should be installed and signal processing should be performed using the resistance detection units. To solve these problems, according to the present invention, a boundary surface between the target fluid A and the reference fluid B is adjusted to fall within the fixed boundary surface measuring units 45 and 46 by installing the fixed boundary surface measuring units 45 and 46 and properly adjusting injection flow rates of the two fluids A and B.

That is, when injection flow rate between the target fluid A and the reference fluid B is properly adjusted so that the boundary between the two fluids A and B can be detected at the fixed boundary surface measuring units 45 and 46, the number of the counting channels 30 filled with the two injected fluids A and B is fixed, and the injection flow rates of the injected target fluid A and the injected reference fluid B may be determined. Therefore, it is possible to measure the viscosity ($m_A$) of the target fluid A using relational expression (8) for the viscosity.

Figure 11:
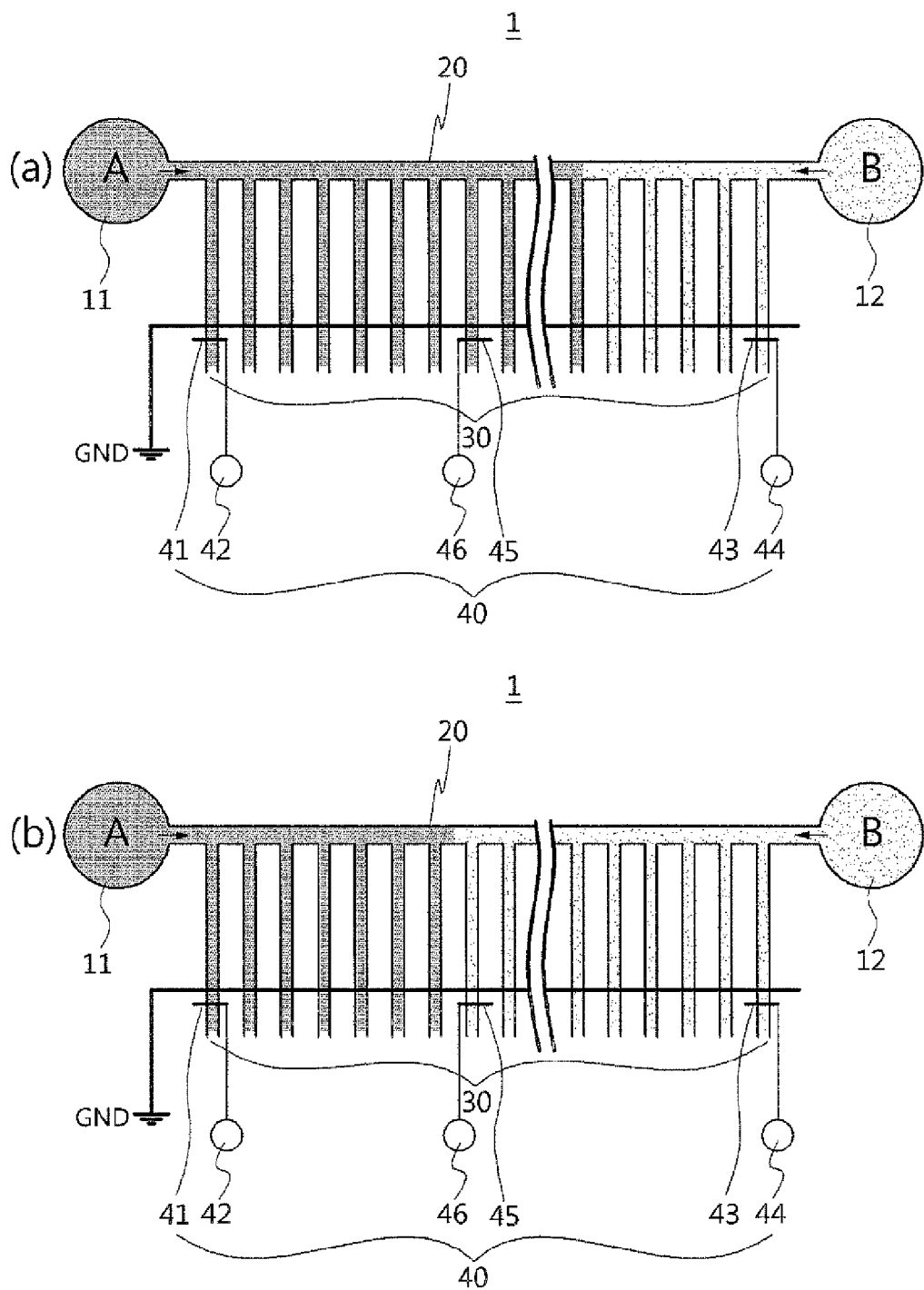
FIG. 11 is a diagram for explaining a method of moving a boundary surface between the target fluid and the reference fluid to a position of an electrode for detecting the boundary surface by adjusting the injection flow rate ratio between the two fluids.
Figure 12:
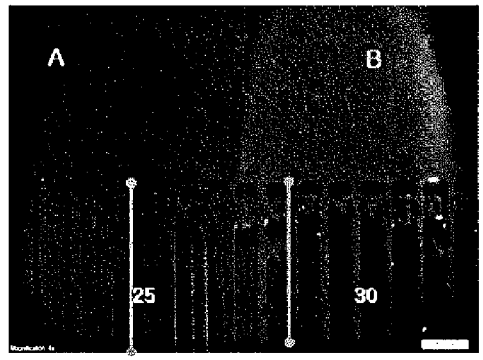
FIG. 12A is a diagram showing the channel number of the counting channels filled with a sodium dodecyl sulfate (SDS) solution having an SDS concentration of 2.5% under the same flow rate condition ($Q_A/Q_B=1,000:1,000$ mL/h)
FIG. 12B is a diagram showing the injection flow rate ($Q_A/Q_B=750:1,000$ mL/h) of the reference fluid when the channel number of the counting channels filled with the reference fluid is 26.
Figure 12:
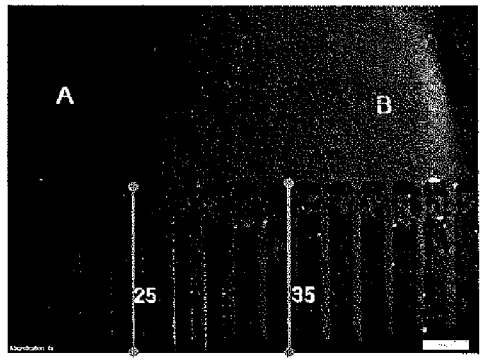
Figure 13:
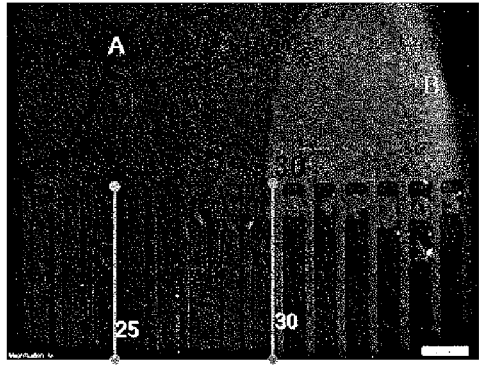
FIG. 13A is a diagram showing the channel number of the counting channels filled with an SDS solution having an SDS concentration of 5.0% under the same flow rate condition ($Q_A/Q_B=1,000:1,000$ mL/h)
FIG. 13B is a diagram showing the injection flow rate ($Q_A/Q_B=620:1,000$ mL/h) of the reference fluid when it is satisfied that the channel number of the counting channels filled with the reference fluid is 26.
Figure 13:
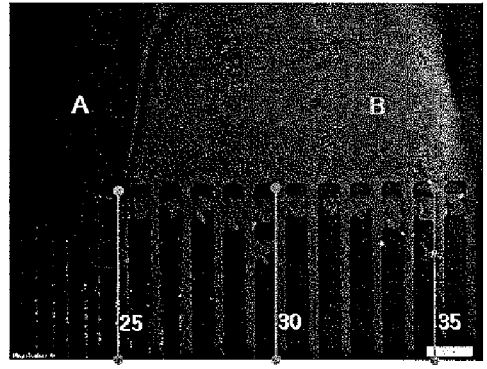
Figure 14:
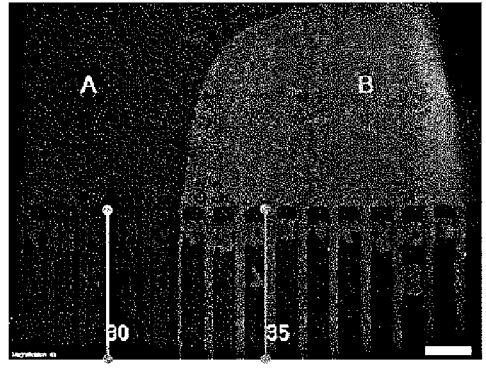
FIG. 14A is a diagram showing the channel number of the counting channels filled with an SDS solution having an SDS concentration of 7.5% under the same flow rate condition ($Q_A/Q_B$=1,000:1,000 mL/h)
FIG. 14B is a diagram showing the injection flow rate ($Q_A/Q_B$=490:1,000 mL/h) of the reference fluid when it is satisfied that the channel number of the counting channels filled with the reference fluid is 26.
Figure 14:
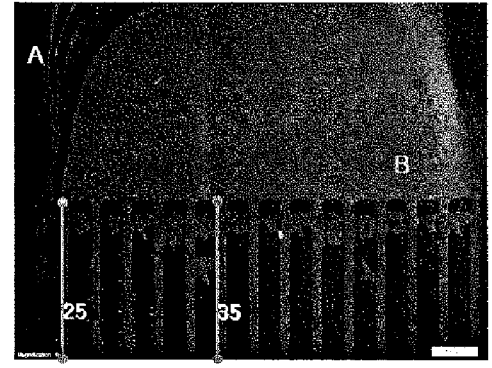
Figure 15:
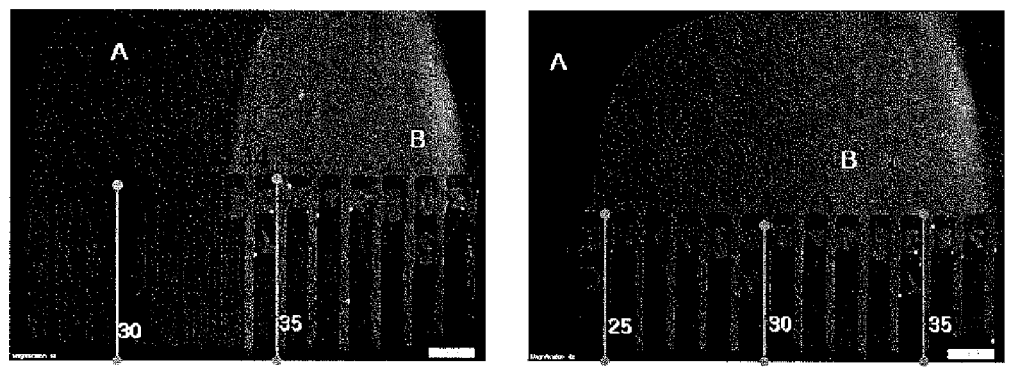
FIG. 15A is a diagram showing the channel number of the counting channels filled with an SDS solution having an SDS concentration of 10.0% under the same flow rate condition ($Q_A/Q_B$=1,000:1,000 mL/h)
FIG. 15B is a diagram showing the injection flow rate ($Q_A/Q_B$=430:1,000 mL/h) of the reference fluid when it is satisfied that the channel number of the counting channels filled with the reference fluid is 26.

FIG. 11 is a diagram for explaining a method of moving a boundary surface between the target fluid and the reference fluid to the fixed boundary surface measuring unit by properly adjusting an injection flow rate ratio between the two fluids.

As shown in FIG. 11A, when the viscosity ($m_A$) of the target fluid A is higher than the viscosity ($m_A$) of the reference fluid B, the boundary surface between the two fluids A and B is present on the right side of the fixed boundary surface measuring units 45 and 46. In this case, the boundary surface between the two fluids A and B may be properly adjusted so that the boundary surface between the two fluids A and B can be detected at the fixed boundary surface measuring units 45 and 46 by decreasing the injection flow rate of the target fluid A, or increasing the injection flow rate of the reference fluid B. On the other hand, when the viscosity ($m_A$) of the target fluid A is lower than the viscosity ($m_B$) of the reference fluid B as shown in FIG. 11B, the boundary surface between the two fluids A and B is present on the left side of the fixed boundary surface measuring units 45 and 46. In this case, when the injection flow rate of the injected target fluid A is increased, or the injection flow rate of the reference fluid B is decreased to move the boundary surface between the two fluids A and B to the fixed boundary surface measuring units 45 and 46, the boundary surface between the two fluids A and B is present in the fixed boundary surface measuring units 45 and 46.

FIGS. 12, 13, 14 and 15 are images taken using DI water as the reference fluid B when SDS is used as the target fluid A at concentrations of 2.5%, 5.0%, 7.5%, and 10.0%, respectively. More particularly, FIGS. 12A, 13A, 14A and 15A show images taken when the flow rate ($Q_A$) of the target fluid A and the flow rate ($Q_B$) of the reference fluid B are each set to 1,000 mL/h, FIGS. 12B, 13B, 14B and 15B show images taken when the injection flow rate ($Q_A$) of the target fluid A is set to 750 mL/h, 620 mL/h, 490 mL/h, and 430 mL/h so as to satisfy that the channel number (NA) of the counting channels 30 filled with the target fluid A is 24.

According to the present invention, a viscosity value of SDS is measured using a conventional HAAKE MARS viscometer for accurate comparison with the experimental results measured for concentrations (2.5%, 5%, 7.5%, and 10%) of SDS. The viscosity values for the experimental results measured using the two viscometers are plotted as the graph shown in FIG. 16.

Figure 16:
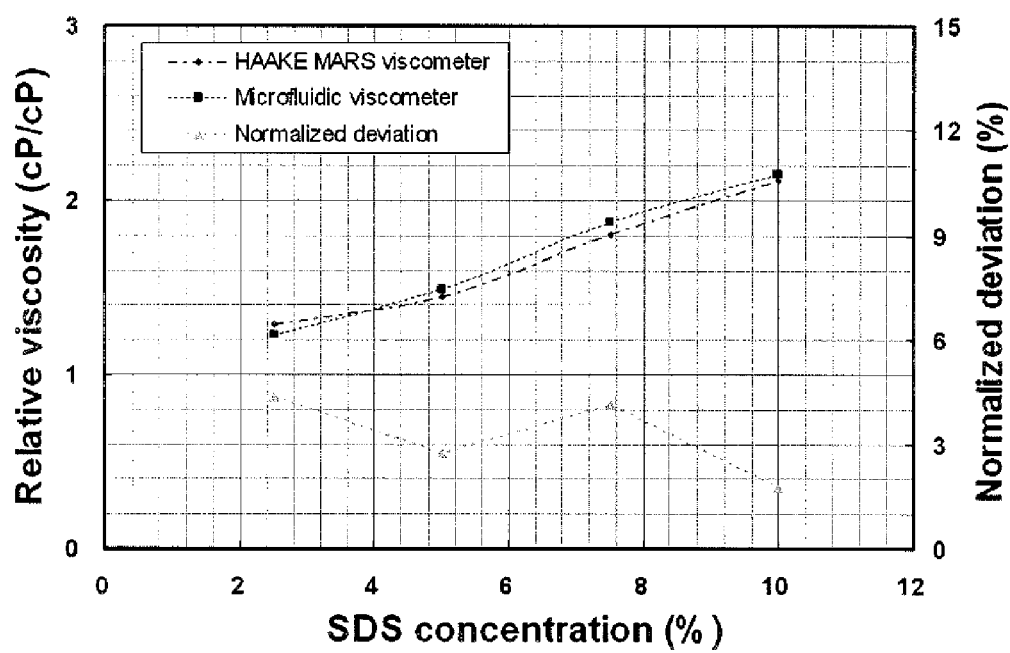
FIG. 16 is a diagram showing viscosity values of four SDS solutions having increasing SDS concentrations (2.5%, 5%, 7.5%, and 10%) as measured using the method proposed in the present invention, the viscosity values of the four SDS solutions as measured using a typical viscometer (conventional HAAKE MARS), and the normalized deviations between the viscosity values obtained using the two viscometers

Referring to FIG. 16, it was revealed that the fluid viscosity measuring device according to the present invention may be used to accurately measure viscosity because the viscosity values measured for 4 concentration of SDS using the fluid viscosity measuring device 1 according to the present invention are highly accurate within 4.0% in average, compared with the viscosity values measured using the conventional HAAKE MARS viscometer.

While the example embodiments of the present invention has been described with reference to the accompanying drawings, it will be understood by those skilled in the art to which the example embodiments of the present invention belongs that the present invention may be embodied in many alternate forms without changing the technical scope or essential features of the invention. It will be understood, however, that the description proposed herein is merely example embodiments for the purpose of illustrations only, not intended to limit the scope of the invention, so that the scope of the present invention is defined by the appended claims rather than the detailed description of the present invention, and intended to cover all modifications, equivalents, and alternatives falling within the scope of the invention.

[Industrial Applicability]

The present invention can be used in various industries using a viscometer such as a microfluidic device that can accurately measure the viscosities of various fluids including a Newtonian fluid as well as a non-Newtonian fluid such as blood.

The invention claimed is:

1. A fluid viscosity measuring device comprising:
a first fluid inlet portion through which a target fluid whose viscosity is to be measured is injected, and a second fluid inlet portion through which a reference fluid having a reference viscosity is injected;
a connection pipe configured to connect the first fluid inlet portion and the second fluid inlet portion with each other, and form passages for the target fluid and the reference fluid;
a plurality of counting channels disposed in communication with the connection pipe at a predetermined distance to be filled with the target fluid and the reference fluid which flow respectively through the passages of the connection pipe; and
a boundary surface measuring unit configured to count the counting channels filled with either the target fluid or the reference fluid.

2. The fluid viscosity measuring device according to claim 1, wherein the counting channels are formed at the connection pipe in a vertical direction.

3. The fluid viscosity measuring device according to claim 1, wherein a normalized relative viscosity ratio between the target fluid and the reference fluid is convergent to 1 by increasing the fluidic resistance ratio between the connection pipe and the counting channels.

4. The fluid viscosity measuring device according to claim 3, wherein fluid resistance of the connection pipe is set to be at least 1,000 times lower than those of the counting channels so that most of the friction loss of the target fluid and the reference fluid takes place in the counting channels.

5. The fluid viscosity measuring device according to claim 1, wherein the viscosity of the target fluid is measured using a number ratio of the counting channels filled with the target fluid and the reference fluid, and an injection flow rate ratio between the target fluid and the reference fluid.

6. The fluid viscosity measuring device according to claim 5, wherein a viscosity coefficient of the target fluid is calculated based on the following mathematical equation:

$$\mu_A = \mu_B \left(\frac{N_A}{N_B}\right)\left(\frac{Q_B}{Q_A}\right)$$

$\mu_A$: a viscosity coefficient of the target fluid
$\mu_A$: a viscosity coefficient of the reference fluid
$N_A$: the number of counting channels filled with the target fluid
$N_B$: the number of counting channels filled with the reference fluid
$Q_A$: an injection flow rate of the target fluid
$Q_B$: an injection flow rate of the reference fluid.

7. The fluid viscosity measuring device according to claim 1, wherein the target fluid includes a non-Newtonian fluid whose viscosity varies according to a shear rate, and the reference fluid includes a Newtonian fluid having a constant viscosity regardless of the shear rate.

8. The fluid viscosity measuring device according to claim 7, wherein the target fluid is blood, and the reference fluid is phosphate buffered saline (PBS).

9. The fluid viscosity measuring device according to claim 1, wherein both the target fluid and the reference fluid include a Newtonian fluid having a constant viscosity regardless of the shear rate.

10. The fluid viscosity measuring device according to claim 9, wherein the target fluid is a sodium dodecyl sulfate (SDS) solution, and the reference fluid is deionized (DI) water.

11. The fluid viscosity measuring device according to claim 1, wherein the boundary surface measuring unit comprises:
a first electrode provided in one of the counting channels filled with the target fluid, and a first resistance detection unit electrically connected with the first electrode to detect resistance of the first electrode;
a second electrode provided in one of the counting channels filled with the reference fluid, and a second resistance detection unit electrically connected with the second electrode to detect resistance of the second electrode; and
a third electrode provided in one of the counting channels arranged between the first electrode and the second electrode so as to detect a fixed boundary surface between the target fluid and the reference fluid while allowing the boundary surface between the two fluids to move by changing the injection flow rate ratio between the two fluids, and a third resistance detection unit electrically connected with the third electrode to detect resistance of the third electrode.

* * * * *